(12) United States Patent
Theobald et al.

(10) Patent No.: US 8,211,874 B2
(45) Date of Patent: Jul. 3, 2012

(54) INHIBITION OF THROMBIN GENERATION

(75) Inventors: Klaus Theobald, Paoli, PA (US);
Jerrold H. Levy, Atlanta, GA (US)

(73) Assignee: Galderma Laboratories Inc., Fort Worth, TX (US)

( * ) Notice: Subject to any disclaimer, the term of this patent is extended or adjusted under 35 U.S.C. 154(b) by 1441 days.

(21) Appl. No.: 11/421,615

(22) Filed: Jun. 1, 2006

(65) Prior Publication Data
US 2007/0004685 A1    Jan. 4, 2007

Related U.S. Application Data

(60) Provisional application No. 60/687,293, filed on Jun. 3, 2005.

(51) Int. Cl.
*A01N 37/18* (2006.01)
*A61K 31/65* (2006.01)
(52) U.S. Cl. ........................ 514/152
(58) Field of Classification Search ........... 514/152
See application file for complete search history.

(56) References Cited

U.S. PATENT DOCUMENTS

2004/0063674 A1 * 4/2004 Levy et al. ............. 514/152
2004/0102388 A1 * 5/2004 High et al. ............. 514/44

OTHER PUBLICATIONS

Stefanini, Mario., "Transient Deficiency of Antihemophilic Factor (AHF) Procoagulant and AHF-like Antigen during Administration of Tetracycline," *A.J.C.P.* Mar. 1980, 73(3):439-443.
Kodama, et al., "Japanese spotted fever associated with multiorgan failure," *J Infect Chemother* 2001, 7:247-250.
Strukova, "Thrombin as a Regulator of Inflammation and Reparative Processes in Tissues," *Biochemistry (Moscow)* 2001, 66(1):8-18.

* cited by examiner

*Primary Examiner* — Yong Chong
(74) *Attorney, Agent, or Firm* — Hoffmann & Baron, LLP

(57) ABSTRACT

The present invention is a method for inhibiting undesirable thrombin generation in a mammal in need thereof. The method comprises administering to the mammal an effective amount of a non-antibacterial tetracycline formulation.

10 Claims, 2 Drawing Sheets

Figure 1A  Actin
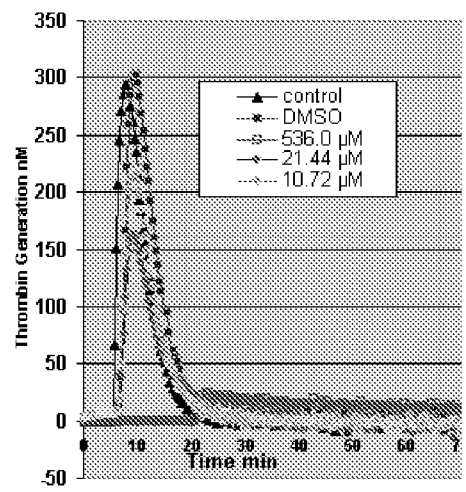
Figure 1B  Innovin
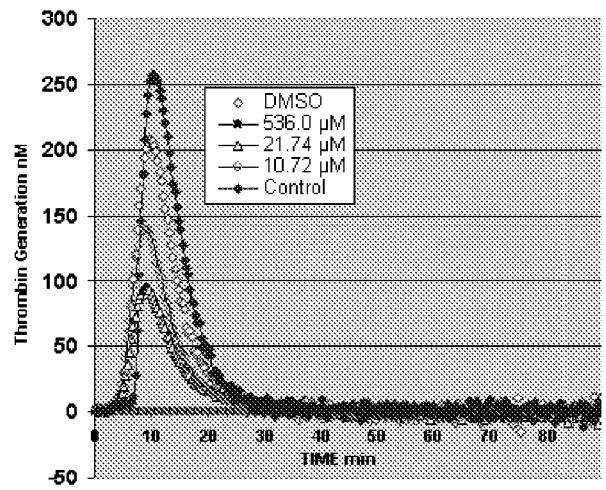

*$p<0.05$ vs. DMSO control

INHIBITION OF THROMBIN GENERATION

This application asserts priority to U.S. Provisional Application Ser. No. 60/687,293 filed on Jun. 3, 2005, the specification of which is hereby incorporated by reference in its entirety.

BACKGROUND OF THE INVENTION

Thrombin is a serine protease belonging to the trypsin family. It is a key enzyme involved in the blood coagulation system.

The coagulation system can be activated in response to surface contact or vascular injury, through either an intrinsic pathway or an extrinsic pathway, respectively. In the intrinsic pathway, all of the protein components involved in coagulation are present in blood. In the extrinsic pathway, by contrast, cell membrane proteins (i.e., tissue factors) are involved in, and play, a critical role.

Typically, the coagulation system is activated in response to vascular injury. The last two steps of the coagulation cascade leading to clot formation are common to both pathways. The first of these two steps involves the conversion of prothrombin to thrombin. This conversion is catalyzed by the enzyme Factor Xa. Thrombin then converts fibrinogen to insoluble fibrin, which is a major component of blood clots.

In addition to thrombin's role in blood coagulation, the formation of thrombin at a site of vascular injury also activates numerous cells involved in inflammatory reactions and tissue reparative processes. Such cells include monocytes, T lymphocytes, fibroblasts, endothelial cells and mast cells. For example, it is reported that thrombin stimulates adhesion and aggregation of platelets, activation of endothelial cells, release of growth factors from cells, and adhesion and recruitment of leukocytes, such as monocytes and T lymphocytes.

Abnormalities in the coagulation cascade have been implicated in numerous vascular diseases and conditions. Such diseases and conditions include cardiovascular diseases (e.g., thrombosis such as deep vein thrombosis, myocardial thrombosis, etc., and peripheral arterial occlusion, coronary artery disease, myocardial ischemia, pulmonary embolism, etc.), cerebrovascular diseases (e.g., stroke such as ischemic stroke and thrombotic stroke). These diseases and conditions are generally characterized by either partial or total occlusion of a blood vessel by a blood clot.

In order to prevent or treat conditions and disorders associated with abnormal coagulation, therapeutic methods to inhibit clot formation or to dissolve clots have been developed. Existing anticoagulants, however, produce side effects. For example, heparin is a widely used anticoagulant drug. Heparin administration, however, can cause bleeding and thrombocytopenia (i.e., decrease in platelets). In addition, heparin has to be injected or infused and the half-life in the circulation is short.

Another class of anticoagulants is that of the coumarins, of which coumadin (referred to generically as warfarin) is commonly used. However, a disadvantage of warfarin is that it takes several days to achieve its maximum effect. As with heparin, bleeding can also be a complication. In addition, warfarin is teratogenic, and can cross the placenta, causing fetal abnormalities when administered to pregnant women.

Thrombolytic agents, which dissolve existing clots, are also used therapeutically. Their activity is based on enhancing the generation of plasmin from its plasminogen precursor. The enzyme plasmin generally dissolves blood clots by specifically cleaving fibrin.

Such thrombolytic agents include recombinant tissue plasminogen activator (tPA) and streptokinase. Disadvantages of these thrombolytics include a systemic fibrinolytic activity that can result in bleeding throughout the body. Further, some thrombolytics (e.g., streptokinase) are antigenic and can cause allergic reactions.

The compound tetracycline is a member of a class of antibiotic compounds that is referred to as the tetracyclines, tetracycline compounds, tetracycline derivatives and the like. The compound tetracycline exhibits the following general structure:

Structure A

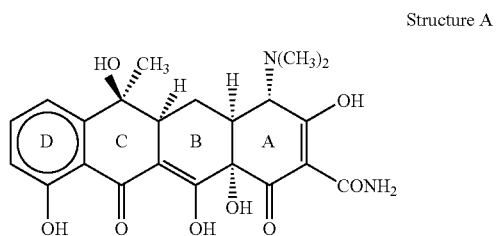

The numbering system of the tetracycline ring nucleus is as follows:

Structure B

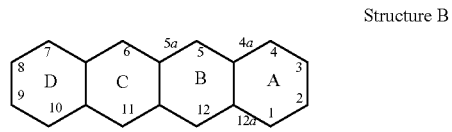

Tetracycline, as well as the terramycin and aureomycin derivatives, exist in nature, and are well known antibiotics. Natural tetracyclines may be modified without losing their antibiotic properties, although certain elements must be retained. The modifications that may and may not be made to the basic tetracycline structure have been reviewed by Mitscher in *The Chemistry of Tetracyclines*, Chapter 6, Marcel Dekker, Publishers New York (1978). According to Mitscher, the substituents at positions 5-9 of the tetracycline ring system may be modified without the complete loss of antibiotic properties.

In addition to their antibacterial properties, tetracyclines have been described as having a number of other uses. For example, tetracyclines are also known to inhibit the activity of collagen destructive enzymes, produced by mammalian (including human) cells and tissues, by non-antibiotic mechanisms. Such enzymes include the matrix metalloproteinases (MMPs), including collagenases (MMP-1, MMP-8 and MMP-13), gelatinases (MMP-2 and MMP-9), and others (e.g., MMP-12, MMP-14). See Golub et al., *J. Periodont. Res.* 20:12-23 (1985); Golub et al. *Crit. Revs. Oral Biol. Med.* 2:297-322 (1991); U.S. Pat. Nos. 4,666,897; 4,704,383; 4,935,411; 4,935,412. Also, tetracyclines have been known to inhibit wasting and protein degradation in mammalian skeletal muscle, U.S. Pat. No. 5,045,538; to inhibit inducible NO synthase, U.S. Pat. Nos. 6,043,231 and 5,523,297; to inhibit phospholipase $A_2$, U.S. Pat. Nos. 5,789,395 and 5,919,775; to inhibit neutrophil elastase, U.S. Pat. No. 5,773,430; and to enhance IL-10 production in mammalian cells, U.S. Pat. No. 6,015,804. These properties cause the tetracyclines to be useful in treating a number of diseases.

It is one object of the present invention to provide a method for inhibiting undesirable thrombin generation. Inhibition of undesirable thrombin generation is useful in diseases and conditions associated with abnormal blood clotting.

SUMMARY OF THE INVENTION

The above need has been met by the present invention which is a method for inhibiting undesirable thrombin generation in a mammal in need thereof. The method comprises administering to the mammal an effective amount of a non-antibacterial tetracycline formulation. The non-antibacterial tetracycline formulation comprises an antibacterial tetracycline in a sub-antibacterial amount, or a non-antibacterial tetracycline.

BRIEF DESCRIPTION OF THE FIGURES

FIGS. 1A and 1B. COL-3 effects on thrombin generation.

DETAILED DESCRIPTION OF THE INVENTION

Figure 2:
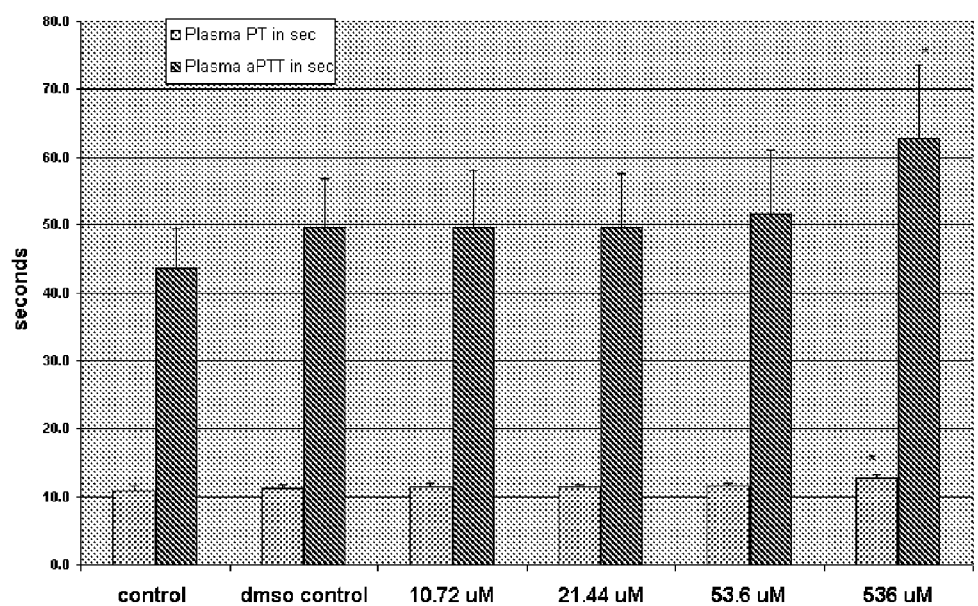
FIG. 2. COL-3 effects on plasma PT and aPTT.

The invention relates to a method for inhibiting undesirable thrombin generation. The method comprises administering an effective amount of a non-antibacterial tetracycline formulation.

The non-antibacterial tetracycline formulations useful in the methods of the present invention can directly or indirectly inhibit the generation of thrombin. For example, the non-bacterial tetracycline formulation can directly inhibit the conversion of prothrombin to thrombin. Alternatively, the non-antibacterial tetracycline formulation can inhibit any step in the blood coagulation cascade involved in thrombin generation.

The phrase "undesirable thrombin generation" as used herein refers to an amount of thrombin produced that is capable of causing the formation of undesirable coagulation. Typically, undesirable coagulation refers to coagulation above normal hemostasis levels or normal coagulation levels (e.g., normal wound healing levels). The formation of undesirable coagulation can result in damage of organs and tissues.

Undesirable thrombin generation is considered to be inhibited if the undesirable generation is reduced by at least about 10%, more preferably at least about 25%, even more preferably at least about 50%, and even more preferably at least about 75%. Most preferably, the undesirable generation of thrombin in a mammal is reduced to substantially normal hemostasis levels or normal coagulation levels.

Inhibiting Undesirable Thrombin Generation

In one embodiment, the non-antibacterial tetracycline formulations of the present invention inhibit undesirable thrombin generation in a mammal in need thereof. Mammals in need of inhibiting undesirable thrombin generation include any mammal which has a disease or condition generally characterized by an undesirable amount of thrombin. The undesirable amount of thrombin generation may damage tissues or organs. Such diseases or conditions include those wherein a blood vessel is partially or totally occluded by a blood clot.

Examples of such diseases and conditions include cardiovascular diseases (e.g., thrombosis such as deep vein thrombosis, myocardial thrombosis, etc.; peripheral arterial occlusion; coronary artery disease; myocardial ischemia; pulmonary embolism, etc.), and cerebrovascular diseases (e.g., stroke such as ischemic stroke and thrombotic stoke). Deep vein thrombosis may occur with or without pulmonary embolism.

Reducing Risk of Undesirable Thrombin Generation

In another embodiment, the non-antibacterial tetracycline formulations of the present invention reduce risk of undesirable thrombin generation in a mammal in need thereof. Mammals in need of reducing risk include humans determined by physicians or other medical experts to be at risk for undesirable thrombin generation. For example, numerous diseases, conditions, activities and medications are associated with a potential for undesirable thrombin generation.

Examples of such diseases and conditions include ischemic complications of unstable angina, and myocardial infraction and stroke, pregnancy, ATIII deficiency, Factor V Leiden, protein S deficiency, hyperhomocysteinaemia, increased prothrombin level, hyperfibrinogenaemia, overweight and obesity. Examples of activities include smoking; sitting or lying for extended periods of time, such as air travel (e.g., international air travel) or bed rest; surgery (e.g., cardiovascular surgery, orthopedic surgery such as hip or knee replacement surgery); surgery recovery; injury recovery; restricted mobility during for example acute or chronic illness; exposure of blood to foreign surfaces (e.g., stents, oxygenators, etc.) during surgery; exposure of blood to renal dialysis equipment; and childbirth. Examples of medications include oral contraceptives and COX-2 inhibitors (e.g., rofecoxib, valdecoxib, celecoxib). Humans with a history of thrombosis are also associated with a potential for undesirable thrombin generation.

The risk is preferably reduced by at least about 10%, more preferably at least about 25%, even more preferably at least about 50%, and even more preferably at least about 75%. Most preferably, the risk in a mammal is eliminated.

Non-antibacterial Tetracycline Formulation

In this specification, a non-antibacterial tetracycline formulation comprises a sub-antibacterial amount of an antibacterial tetracycline compound, a non-antibacterial tetracycline compound, or a pharmaceutically acceptable salt thereof.

Any antibacterial tetracycline compound may be used in the methods of the present invention. Some examples of antibacterial tetracycline compounds include doxycycline, minocycline, tetracycline, oxytetracycline, chlortetracycline, demeclocycline, lymecycline. Doxycycline is preferably administered as its hyclate salt or as a hydrate, preferably monohydrate.

Non-antibacterial tetracycline compounds are structurally related to the antibacterial tetracyclines, but have had their antibacterial activity substantially or completely eliminated by chemical modification. For example, non-antibacterial tetracycline compounds have at least about ten times, preferably at least about twenty five times, less antibacterial activity than that of doxycycline. In other words, non-antibacterial tetracycline compounds are incapable of achieving antibacterial activity comparable to that of doxycycline at concentrations at least about ten times, preferably at least about twenty five times, greater than that of doxycycline.

Any non-antibacterial tetracycline compound may be used in the methods of the present invention. Some examples include those compounds disclosed generically or specifically in U.S. Pat. No. 6,638,922 issued on Oct. 28, 2003, and assigned to CollaGenex Pharmaceuticals, Inc. The tetracycline compounds disclosed in U.S. Pat. No. 6,638,922 are herein incorporated by reference.

Other examples of non-antibacterial tetracycline compounds (COLs) include 4-de(dimethylamino)tetracycline (COL-1), tetracyclinonitrile (COL-2), 7-chloro-4-de(dimethylamino)-tetracycline (COL-4), tetracycline pyrazole (COL-5), 4-hydroxy-4-de(dimethylamino)-tetracycline (COL-6), 4-de(dimethylamino-12a-deoxytetracycline (COL-7), and 4-de(dimethylamino)-12a-deoxyanhydrotetracycline (COL-9).

Tetracycline compounds are either isolated from nature, or are prepared by any method known in the art. For example, natural tetracyclines may be modified without losing their antibacterial properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5-9 of the tetracycline ring system may be modified without the complete loss of antibacterial properties. Changes to the basic ring system or replacement of the substituents at positions 1-4 and 10-12, however, generally lead to tetracyclines with substantially less or effectively no antibacterial activity.

The term "pharmaceutically acceptable slat" refers to a salt prepared from a well-tolerated, nontoxic tetracycline compound, and an acid or base. The acids may be inorganic or organic acids of antibacterial tetracycline compounds or non-antibacterial tetracycline compounds. Examples of inorganic acids include hydrochloric, hydrobromic, nitric hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids. Appropriate organic bases may be selected for example, from N,N-dibenzylethylenediamine, chloroprocaine, choline, diethanolamine, ethylenediamine, meglumine (N-methylglucamine), and procaine.

Throughout this specification, parameters are defined by maximum and minimum amounts. Each minimum amount can be combined with each maximum amount to define a range.

Dose

According to the present invention, a non-antibacterial tetracycline formulation comprising an antibacterial tetracycline compound is administered in a sub-antibacterial amount. A sub-antibacterial amount of an antibacterial tetracycline compound is any amount that results in a tetracycline plasma concentration: (i) which is effective for inhibiting undesirable thrombin generation, but (ii) which has no, or substantially no, antibacterial activity.

A concentration of an antibacterial tetracycline compound having substantially no antibacterial activity is any concentration that does not significantly prevent the growth of bacteria. That is, a microbiologist would not consider the growth of bacteria to be inhibited from a clinical point of view.

One way in which to quantify the antibacterial activities of tetracyclines is by a measure called minimum inhibitory concentration (MIC), as is known by a skilled artisan.

An MIC is the minimum tetracycline concentration that inhibits the growth of a particular strain of bacteria in vitro. MIC values are determined using standard procedures. Standard procedures are, for example, based on a dilution method (broth or agar), or an equivalent, using standard concentrations of inoculum and tetracycline powder. See, for example, National Committee for clinical Laboratory Standards. *Performance Standards for Antimicrobial Susceptibility Testing—Eleventh Informational Supplement*. NCCLS Document M100-S11, Vol. 21, No. 1, NCCLS, Wayne, Pa., January, 2001.

In order to inhibit the growth of a strain of bacteria in vivo, a tetracycline compound achieves a plasma concentration in excess of the MIC for the strain. Plasma concentration refers to the concentration of a tetracycline compound measured in an individual's blood sample taken at steady state. Steady state is generally achieved after dosing for five to seven terminal half lives. The half lives of different tetracycline compounds vary from hours to days.

In the present invention, an antibacterial tetracycline compound is administered in an amount that is effective, as described above, and that results in a plasma concentration which is significantly below the MIC for commonly-occurring bacteria. Such amounts are considered to have no, or substantially no, antibacterial activity. Examples of commonly-occurring bacteria that are susceptible to tetracyclines are *Escherichia coli* (e.g., ATCC25922); *Neisseria gonorrhoeae* (e.g., ATCC 49226); *Staphylococcus aureus* (e.g., ATCC 29213 and 25213); and *Streptococcus pneumoniae* (e.g., ATCC 49619).

For example, in the present invention, an antibacterial tetracycline compound is administered in an amount that results in a plasma concentration which is less than approximately 80%, 75%, 70%, 65%, 60%, 55%, 50%, 45%, 40%, 35%, 30%, 25%, 20%, 15%, 10%, 5%, 1% or 0.5% of the MIC for the commonly-occurring bacteria mentioned above. A skilled artisan can readily determine the amount of a particular antibacterial tetracycline compound to administer to achieve such concentrations.

For example, doxycycline is administered in an amount that results in a minimum steady state plasma concentration of about 0.1 µg/ml, 0.2 µg/ml, or 0.3 µg/ml, and a maximum steady state plasma concentration of about 0.7 µg/ml, 0.8 µg/ml, or 0.9 µg/ml.

The sub-antibacterial amount of an antibacterial tetracycline compound can also be expressed by daily dose. The daily dose of an antibacterial tetracycline compound is any amount that is sufficient to produce the effective, sub-antibacterial plasma concentrations described above. Such dose can, for example, be expressed as a percentage of a minimum antibacterial daily dose.

A skilled artisan knows, or is able routinely to determine, the minimum antibacterial daily dose for antibacterial tetracycline compounds. Examples of suitable sub-antibacterial doses of antibacterial tetracycline compounds for the methods of the present invention include less than approximately: 80%, 75%, 70%, 65%, 60%, 55%, 50%, 45%, 40%, 35%, 30%, 25%, 20%, 15%, 10%, 5%, 1% and 0.5% of a minimum antibacterial dose.

Some examples of non-antibacterial daily doses of antibacterial tetracycline compounds include about 20 mg/twice a day of doxycycline; about 38 mg of minocycline one, two, three or four times a day; and about 60 mg of tetracycline one, two, three or four times a day.

There is no necessary minimum effective amount of the antibacterial tetracycline compound, as long as the amount administered is capable of inhibiting undesirable thrombin generation. For example, when the amount is expressed as a percentage of the MIC plasma concentration, suitable minimum plasma concentrations include approximately 0.1%, 0.5%, 0.8% and 1% of the MIC plasma concentration. When the amount is expressed as a minimum actual plasma concentration, suitable actual plasma concentrations include approximately 0.01 µg/ml, 0.05 µg/ml, 0.1 µg/ml, 0.15 µg/ml, 0.2 µg/ml, 0.25 µg/ml and 0.3 µg/ml. When the dose is expressed as a percentage of a minimum antibacterial daily dose, the percentage is approximately 0.1%, 0.2%, 0.5%, 1%, 1.5% and 2% of the minimum antibacterial dose.

In an embodiment, any form of doxycycline (e.g., doxycycline salts, such as doxycycline hyclate; and doxycycline hydrates, such as doxycycline monohydrate) is administered in a daily amount of, or equivalent to, from about 10 to about 60 milligrams of doxycycline, while maintaining a concentration in human plasma below the MIC.

In an especially preferred embodiment, doxycycline, a doxycycline salt, or a doxycycline hydrate, is administered at a dose of, or equivalent to, 20 milligram of doxycycline twice daily. Such a formulation is sold for the treatment of periodontal disease by CollaGenex Pharmaceuticals, Inc. of Newtown, Pa. under the trademark Periostat®.

A non-antibacterial tetracycline formulation comprising a non-antibacterial tetracycline compound, such as the COLs discussed above, is administered at any effective dose at which side effects, if any, are acceptable since non-antibacterial tetracycline compounds have no, or substantially no, antibacterial activity. Therefore, there is no risk of indiscriminate killing of bacteria, and the resulting threat of developing resistant bacteria.

For example, suitable maximum plasma concentrations of the COLs mentioned above include up to about 100 µg/ml, about 200 µg/ml and about 300 µg/ml. Suitable maximum daily doses of COLs include about 18 mg/kg/day, about 40 mg/kg/day, about 60 mg/kg/day and about 80mg/kg/day.

A preferred COL is 6-demethyl-6-deoxy-4-de(dimethylamino)tetracycline (COL-3). COL-3 is administered in doses of up to about 200 mg/day, preferably about 150 mg/day, more preferably about 100 mg/day, or in amounts that result in plasma concentrations of up to about 50 µg/ml, about 40 µg/ml or about 30 µg/ml. For example, a dose of about 10 to about 20 mg/day of COL-3 produces plasma concentrations in humans of about 1.0 µg/ml.

There is no necessary minimum effective dose of COLs. Some typical minimum plasma concentrations of COLs include, for example, about 0.01 µg/ml, 0.1 µg/ml, 0.8 µg/ml and 1.0 µg/ml. Some typical minimum daily doses of COLs include about 0.05 mg/kg/day, about 0.1 mg/day, about 0.5 mg/day, about 1 mg/day, about 5 mg/day, or about 10 mg/day.

An advantage of non-antibacterial formulations useful in the methods of the present invention is that they are administered at a dose which avoids side effects, such as the development of antibiotic resistant bacteria. Antibiotics are normally administered to a mammal for a period of about eight to twelve days, and usually not more than about two weeks.

The non-antibacterial tetracycline formulations can more safely be administered for periods longer than antibiotic compounds. For example, the non-antibacterial tetracycline formulations can be administered for at least about three weeks, preferably at least about six weeks, more preferably at least about two months, and most preferably at least about six months. Optimally, the non-antibacterial tetracycline formulations can be administered for at least about one year.

Phototoxicity

Preferably, the tetracycline compounds have low phototoxicity, or are administered in an amount that results in a plasma level at which the phototoxicity is acceptable. A preferred amount of the tetracycline compound produces no more phototoxicity than is produced by the administration of a 40 mg total daily dose of doxycycline.

Examples of tetracycline compounds with low phototoxicity include, but are not limited to, tetracycline compounds having general formulae:

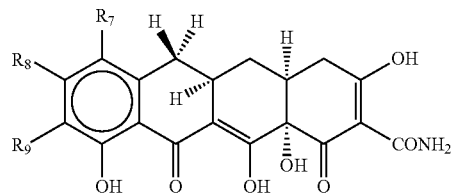

Structure K wherein: R7, R8, and R9 taken together in each case, have the following meanings:

| R7 | R8 | R9 | |
|---|---|---|---|
| hydrogen | hydrogen | amino (COL-308) | |
| hydrogen | hydrogen | palmitamide (COL-311) | |
| hydrogen | hydrogen | dimethylamino (COL-306) | and |

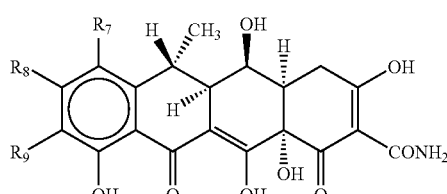

Structure L

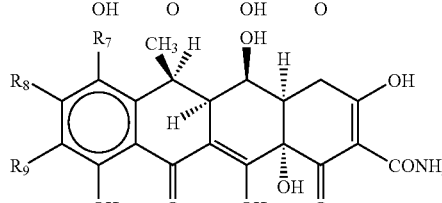

Structure M

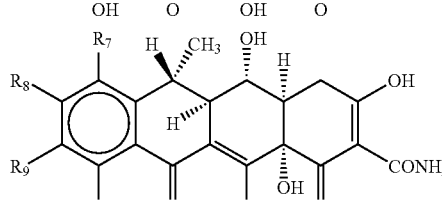

Structure N

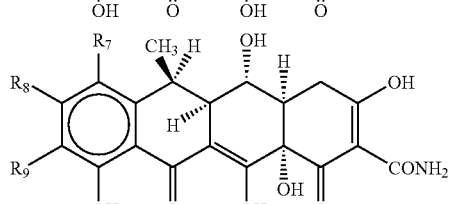

Structure O wherein: R7, R8, and R9 taken together in each case, have the following meanings:

| R7 | R8 | R9 | |
|---|---|---|---|
| hydrogen | hydrogen | acetamido (COL-801) | |
| hydrogen | hydrogen | dimethylaminoacetamido (COL-802) | |
| hydrogen | hydrogen | palmitamide (COL-803) | |
| hydrogen | hydrogen | nitro (COL-804) | |
| hydrogen | hydrogen | amino (COL-805) | and |

-continued

| R7 | R8 | R9 |
|----|----|----|

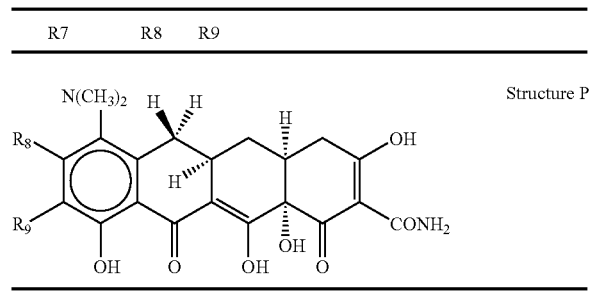

Structure P wherein: R8, and R9 taken together are, respectively, hydrogen and nitro (COL-1002).

Administration

The non-antibacterial tetracycline formulation may be administered by any method known in the art. The actual preferred amounts of a non-antibacterial tetracycline formulation in a specified case will vary according to the particular tetracycline compound used, the mode of application, the particular sites of application, and the subject being treated (e.g., age, gender, size, tolerance to drug, etc.)

The non-antibacterial tetracycline formulation may be administered systemically. For the purposes of this specification, "systemic administration" means administration to a human by a method that causes the compounds to be absorbed into the bloodstream.

Preferably, the non-antibacterial tetracycline formulation is administered orally by any method known in the art. For example, the non-antibacterial tetracycline formulation can be administered in the form of tablets, capsules, pills, troches, elixirs, suspensions, syrups, wafers, chewing gum and the like.

Additionally, the non-antibacterial tetracycline formulations can be administered enterally or parenterally, e.g., intravenously; intramuscularly; subcutaneously, as injectable solutions or suspensions; intraperitoneally; or rectally. Administration can also be intranasally, in the form of, for example, an intranasal spray; or transdermally, in the form of, for example, a patch.

For the pharmaceutical purposes described above, the non-antibacterial tetracycline formulations useful in the methods of the invention can be formulated per se in pharmaceutical preparations optionally with a suitable pharmaceutical carrier (vehicle) or excipient as understood by practitioners in the art. These preparations can be made according to conventional chemical methods.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the non-antibacterial tetracycline formulations can be employed, and the pH of the solutions can be suitably adjusted and buffered. For intravenous use, the total concentration of the solute(s) can be controlled in order to render the preparation isotonic.

The non-antibacterial tetracycline formulation of the present invention can further comprise one or more pharmaceutically acceptable additional ingredient(s) such as alum, stabilizers, buffers, coloring agents, flavoring agents, and the like.

The non-antibacterial tetracycline formulation may be administered at intervals. For example, the non-antibacterial tetracycline formulation may be administered 1-6 times a day, preferably 1-4 times a day.

In an embodiment the non-antibacterial tetracycline formulation containing any of the above described doses of any antibacterial tetracycline compounds or non-antibacterial tetracycline compounds, such as those mentioned above. e.g., doxycycline and COL-3, is administered by controlled release over a particular period of time, such as a 24 hour period. The level is typically measured by plasma concentration. For example, doxycycline is preferably administered in an amount of about 40 milligrams over the 24 hour period. Methods for controlled release of drugs are well known in the art, and are described in, for example, international patent application PCT/US02/10748, which is assigned to CollaGenex Pharmaceuticals, Inc. Newtown, Pa.

The non-antibacterial tetracycline formulation can also be administered topically. The appropriate dose of the non-antibacterial tetracycline formulation for topical administration can be readily determined by those skilled in the art. For example, topical administration of COLs in amounts of up to about 25% (w/w) in a vehicle can be administered without any toxicity in a human. Amounts from about 0.1% to about 10% are preferred.

Particular non-antibacterial tetracycline compounds have only limited biodistribution, e.g., COL-5. In such cases, topical application is the preferred method of administration of the compound.

Carrier compositions deemed to be suited for topical use include gels, salves, lotions, creams, ointments, and the like. The non-antibacterial tetracycline compound can also be incorporated into a support base, matrix, tissue adhesive, or the like which can be directly applied to, for example, skin.

Combined or coordinated topical and systemic administration of the non-antibacterial tetracycline formulation is also contemplated under the invention. For example, a non-absorbable non-antibacterial tetracycline compound can be administered topically, while an antibacterial or non-antibacterial tetracycline compound capable of substantial absorption and effective systemic distribution in a human can be administered systemically.

In one embodiment, the non-antibacterial tetracycline formulation is administered as a pharmaceutical composition comprising an active ingredient consisting essentially of an antibacterial tetracycline compound or a non-antibacterial tetracycline compound in an amount that is effective to achieve its purpose.

Mammals

Any mammal can be treated in accordance with the present invention. Mammals include, for example, humans, baboons, and other primates, as well as pet animals such as dogs and cats, laboratory animals such as rats and mice, and farm animal such as horses, sheep, and cows.

EXAMPLES

Example 1

Inhibition of Thrombin Generation

COL-3 was dissolved in DMSO (dimethyl sulfoxide, Sigma, St. Louis, Mo.). Blood was drawn from 5 consented healthy volunteers into 3.2% citrate tubes.

For TEG (Thromboelastograph, Haemoscope Corp, Skokie Ill.) whole blood samples (0.34 ml) were added to cups along with 10 µl of saline (control), DMSO, or COL-3 (final concentration of 10.72 or 21.44 µM). After addition of calcium chloride (20 µl of 0.2 M), samples were activated with TF (tissue factor) (4 pM) and TEGs (thrombelastogram) were run according to manufacturers directions.

Maximum amplitude (MA), angle, and R-value were recorded. For prothrombin time (PT) and activated partial thromboplastin time (aPTT) blood samples were centrifuged for 15 min at 3000× g to obtain plasma and COL-3 was added to a final concentration of 10.72, 21.44 and 536 µM. Testing was done using Start 4instrument (Diagnostic Stago, Parsippainy, N.J.) along with appropriate standards and controls.

For platelet aggregation studies platelet rich and platelet poor plasma was separated by centrifugation. All platelet studies were performed in a total volume of 500 µl with 200,000 platelets/µl. Platelet aggregation was quantitated by measuring changes in light transmittance in dual channel aggregometer (Chronolog Corp. Havertown, Pa.) using ADP (adenosine di-phosphate) and collagen (final concentration 20 µM) as activators.

For thrombin generation experiments 80 µl of platelet poor plasma containing either saline, DMSO or COL-3 at final concentration of 10.72, 21.44 and 536 µl and thrombin generation trigger (Innovin 5 pM, or Actin 1:20 dilution, Dade Behring, Marburg, Germany) were added to 96 well microtiter plate (Microfluor-2, Thermolabsystems, Franklin Mass.) followed by 20 µl of calcium-substrate (Z-GGR-AMC, Bachem, Switzerland) buffer. The reaction was monitored by measuring increase in fluorescence at 390 nm excitation and 460 nm emission wavelengths and the acquired data was processed for lag time and peak thrombin generation parameters using Thrombinoscope software (Thrombinoscope BV, Maastricht, the Netherlands). The data were imported into excel file and the % decrease in thrombin generation due to COL-3 was calculated. Data were analyzed using repeated ANOVA $p<0.05$ was considered significant.

COL-3 had no effect on platelet aggregation or any of the TEG parameters COL-3 caused a dose dependent reduction in thrombin generation (FIGS. 1A and 1B). PT and aPTT values increased only at the highest concentration of COL-3 levels (FIG. 2).

What is claimed is:

1. A method for inhibiting undesirable thrombin generation in a mammal in need thereof, the method comprising administering to the mammal an effective amount of a non-antibacterial tetracycline formulation wherein the non-antibacterial tetracycline formulation comprises an antibacterial tetracycline in a sub-antibacterial amount, and the antibacterial tetracycline is doxycycline, minocycline, or tetracycline.

2. A method according to claim 1, wherein the antibacterial tetracycline is minocycline.

3. A method according to claim 1, wherein the antibacterial tetracycline is doxycycline.

4. A method according to claim 1, wherein the mammal is human.

5. A method according to claim 1, wherein the non-antibacterial tetracycline formulation inhibits the undesirable conversion of prothrombin to thrombin.

6. A method for reducing risk of undesirable thrombin generation in a mammal in need thereof, the method comprising administering to the mammal an effective amount of a non-antibacterial tetracycline formulation, wherein the tetracycline formulation comprises an antibacterial tetracycline in a sub-antibacterial amount, and the antibacterial tetracycline is doxycycline, minocycline, or tetracycline.

7. A method according to claim 6, wherein the antibacterial tetracycline is minocycline.

8. A method according to claim 6, wherein the antibacterial tetracycline is doxycycline.

9. A method according to claim 6, wherein the mammal is human.

10. A method according to claim 6, wherein the non-antibacterial tetracycline formulation inhibits the undesirable conversion of prothrombin to thrombin.

* * * * *